(12) United States Patent
Saito

(10) Patent No.: US 10,813,541 B2
(45) Date of Patent: Oct. 27, 2020

(54) ENDOSCOPIC DIAGNOSIS APPARATUS, IMAGE PROCESSING METHOD, PROGRAM, AND RECORDING MEDIUM

(71) Applicant: FUJIFILM Corporation, Tokyo (JP)

(72) Inventor: Takaaki Saito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 567 days.

(21) Appl. No.: 15/688,879

(22) Filed: Aug. 29, 2017

(65) Prior Publication Data

US 2017/0354320 A1 Dec. 14, 2017

Related U.S. Application Data

(63) Continuation of application No. PCT/JP2016/054787, filed on Feb. 19, 2016.

(30) Foreign Application Priority Data

Mar. 25, 2015 (JP) .................................. 2015-062725

(51) Int. Cl.
*A61B 1/05* (2006.01)
*A61B 1/00* (2006.01)
(Continued)

(52) U.S. Cl.
CPC ............ *A61B 1/05* (2013.01); *A61B 1/00009* (2013.01); *A61B 1/00089* (2013.01);
(Continued)

(58) Field of Classification Search
CPC ....... A61B 1/04; A61B 1/0661; A61B 1/0676; A61B 1/00009; A61B 1/00089;
(Continued)

(56) References Cited

U.S. PATENT DOCUMENTS 8,827,896 B2 9/2014 Tsuruta et al.
2002/0026093 A1 2/2002 Ooyatsu
(Continued)

FOREIGN PATENT DOCUMENTS

EP 0403399 12/1990
JP S63-49127 3/1988
(Continued)

OTHER PUBLICATIONS

"Search Report of European Counterpart Application" dated Feb. 20, 2018, p. 1-p. 6.
(Continued)

*Primary Examiner* — Matthew J Kasztejna
(74) *Attorney, Agent, or Firm* — JCIPRNET

(57) ABSTRACT

There are provided an endoscopic diagnosis apparatus, image processing method, and recording medium that enable easy measurement of the size of a lesion portion or the like based on an endoscopic image captured through a normal operation without a special operation. A region detecting unit detects, from an endoscopic image, a region of an artificial object or the like that is in contact with a subject. An imaging size calculating unit calculates, in number of pixels, an imaging size in the endoscopic image of the region of the artificial object or the like that is in contact with the subject. A pixel size calculating unit calculates an actual size corresponding to one pixel. A scale generating unit generates scales indicating an actual size of the subject in the endoscopic image. A control unit performs control to combine the endoscopic image and the scales and to display.

15 Claims, 6 Drawing Sheets

(51) Int. Cl.
*A61B 1/018* (2006.01)
*G02B 23/24* (2006.01)
*A61B 1/045* (2006.01)

(52) U.S. Cl.
CPC .......... *A61B 1/00091* (2013.01); *A61B 1/018* (2013.01); *A61B 1/045* (2013.01); *G02B 23/2469* (2013.01)

(58) Field of Classification Search
CPC ............ A61B 1/00101; A61B 1/00096; A61B 1/00091; A61B 1/00094; A61B 5/1079
See application file for complete search history.

(56) References Cited

U.S. PATENT DOCUMENTS

| | | | |
|---|---|---|---|
| 2013/0345513 A1* | 12/2013 | Tsuruta | A61B 1/043 600/117 |
| 2014/0296866 A1 | 10/2014 | Salman et al. | |
| 2015/0287192 A1 | 10/2015 | Sasaki | |

FOREIGN PATENT DOCUMENTS

| | | |
|---|---|---|
| JP | 2002-153421 | 5/2002 |
| JP | 2005-118107 | 5/2005 |
| JP | 2008-245838 | 10/2008 |
| JP | 2011-183000 | 9/2011 |
| JP | 2013-248353 | 12/2013 |
| WO | 2013121610 | 8/2013 |
| WO | 2014097702 | 6/2014 |

OTHER PUBLICATIONS

"Office Action of Japan Counterpart Application," dated Dec. 5, 2017, with English translation thereof, p. 1-p. 7.

"International Search Report (Form PCT/ISA/210) of PCT/JP2016/054787", with English translation thereof, dated May 24, 2016, pp. 1-4.

"Written Opinion (Form PCT/ISA/237) of PCT/JP2016/054787", dated May 24, 2016, with English translation thereof, pp. 1-10.

* cited by examiner

ENDOSCOPIC DIAGNOSIS APPARATUS, IMAGE PROCESSING METHOD, PROGRAM, AND RECORDING MEDIUM

CROSS-REFERENCE TO RELATED APPLICATIONS

This application is a Continuation of PCT International Application No. PCT/JP2016/054787 filed on Feb. 19, 2016, which claims priority under 35 U.S.C. § 119(a) to Japanese Patent Application No. 2015-062725 filed on Mar. 25, 2015. Each of the above application(s) is hereby expressly incorporated by reference, in its entirety, into the present application.

BACKGROUND OF THE INVENTION

1. Field of the Invention

The present invention relates to an endoscopic diagnosis apparatus having a function of measuring the size of a lesion portion or the like in the case of inserting an endoscope into a subject and observing the inside of the subject, and to an image processing method, and a non-transitory computer-readable recording medium.

2. Description of the Related Art

An endoscopic diagnosis apparatus is used to observe the inside of a subject. In the case of observing the inside of a subject, an endoscope is inserted into a body cavity of the subject, white light, for example, is emitted from a distal end portion of the endoscope onto a region of interest, reflected light thereof is received, and thereby an endoscopic image is captured. The captured endoscopic image is displayed on a display unit and observed by an operator of the endoscopic diagnosis apparatus.

There is a demand for measuring the size of a lesion portion such as a tumor portion for the purpose of, for example, removing a tumor if the tumor is larger than a predetermined size and conserving the tumor for monitoring if the tumor has the predetermined size or less, as well as determining the presence or absence of a lesion portion by viewing an endoscopic image captured inside a subject.

A method for measuring the size of a lesion portion by using a surgical instrument such as measuring forceps is known. In this method, measuring forceps are inserted from a forceps inlet of an endoscope and are protruded from a forceps outlet at a distal end portion of the endoscope. A tip portion of the measuring forceps has scales for measuring size. The tip portion, which is flexible, is pressed against a region of interest so as to bend, and the scales on the tip portion are read to measure the size of a tumor or the like in the region of interest.

In this method, however, inserting the measuring forceps into a forceps channel of the endoscope is required only for measuring the size of a lesion portion. This operation is not only time-consuming but also complex and cumbersome. Furthermore, since the measurement is performed by pressing the tip portion of the measuring forceps against a region of interest of a subject so as to bend the tip portion, measurement accuracy is low. In some portions of a subject, it may be difficult to perform measurement, that is, it may be difficult to press the tip portion against the region of interest of the subject.

The related art documents related to the present invention include JP2011-183000A (hereinafter referred to as PTL 1) and JP2008-245838A (hereinafter referred to as PTL 2).

PTL 1 relates to an endoscope apparatus. PTL 1 describes ejecting water streams onto a lesion portion from two openings at a distal end portion of an insertion section of an endoscope and determining, on the basis of the distance between the two water streams being equal to the distance between the two openings, whether or not the lesion portion is larger than or equal to a treatment reference value.

PTL 2 relates to a robotic arm system mounted on an endoscope apparatus. PTL 2 describes setting a plurality of measurement points around a lesion portion by using a tip portion of a surgical instrument or the like, and obtaining the size of the lesion portion through computation on the basis of coordinate information on the measurement points.

SUMMARY OF THE INVENTION

The endoscope apparatus according to PTL 1 involves an issue that a special endoscope including two openings for ejecting two water streams from the distal end portion of the insertion section is required, and that only this endoscope is capable of measuring the size of a lesion portion.

The endoscope apparatus according to PTL 2 involves an issue that a robot arm is required to measure the size of a lesion portion, and that it is necessary to set a plurality of measurement points around the lesion portion by operating the complex robot arm.

An object of the present invention is to solve the issues according to the related art and to provide an endoscopic diagnosis apparatus, image processing method, and a non-transitory computer-readable recording medium that enable easy measurement of the size of a lesion portion or the like based on an endoscopic image captured through a normal operation without a special operation.

To achieve the object, the present invention provides an endoscopic diagnosis apparatus including an imaging unit that captures an endoscopic image of a subject from a distal end portion of an endoscope; a display unit that displays the endoscopic image; a region detecting unit that detects, from the endoscopic image, a region of an artificial object that extends outward from the distal end portion of the endoscope and is in contact with the subject or a region of a water jet that is ejected from an ejection opening at the distal end portion of the endoscope and is in contact with the subject; an imaging size calculating unit that calculates, in number of pixels, an imaging size of the region of the artificial object or the water jet that is in contact with the subject in the endoscopic image; a size information holding unit that holds information of an actual size of the region of the artificial object or the water jet that is in contact with the subject; a pixel size calculating unit that calculates an actual size corresponding to one pixel of the endoscopic image on the basis of the imaging size and the information of the actual size; a scale generating unit that generates scales indicating an actual size of the subject in the endoscopic image on the basis of the actual size corresponding to the one pixel of the endoscopic image; and a control unit that performs control to combine the endoscopic image and the scales and to display, on the display unit, the endoscopic image and the scales that have been combined.

Preferably, the artificial object is a hood that is cylindrical-shaped and has opening portions at both ends thereof, one of the opening portions being fitted and attached to the distal end portion of the endoscope, the region detecting unit detects, from the endoscopic image, the other opening portion of the hood that is in contact with the subject, the imaging size calculating unit calculates, in number of pixels, an imaging size of the other opening portion of the hood that is in contact with the subject in the endoscopic image, and the size information holding unit holds information of an actual size of the other opening portion of the hood that is in contact with the subject.

Preferably, the region detecting unit detects the other opening portion of the hood that is in contact with the subject by extracting a circular edge from a peripheral portion of the endoscopic image.

Preferably, the artificial object is a surgical instrument that extends outward from a forceps outlet at the distal end portion of the endoscope, the region detecting unit detects, from the endoscopic image, a tip portion of the surgical instrument that is in contact with the subject, the imaging size calculating unit calculates, in number of pixels, an imaging size of the tip portion of the surgical instrument that is in contact with the subject in the endoscopic image, and the size information holding unit holds information of an actual size of the tip portion of the surgical instrument.

Preferably, the region detecting unit detects the tip portion of the surgical instrument that is in contact with the subject by extracting, from the endoscopic image, a region in which the surgical instrument extends, on the basis of a position and direction in which the surgical instrument extends in the endoscopic image, the position and direction being determined in accordance with a positional relationship between an observation window and the forceps outlet at the distal end portion of the endoscope.

Preferably, the region detecting unit detects the tip portion of the surgical instrument that is in contact with the subject in accordance with a difference in a ratio of pixel values of individual pixels between the subject and a region in which the surgical instrument extends in a spectral image having two color components of the endoscopic image.

Preferably, the region detecting unit detects, from the endoscopic image, the region of the water jet that is in contact with the subject, the imaging size calculating unit calculates, in number of pixels, the imaging size of the region of the water jet that is in contact with the subject in the endoscopic image, and the size information holding unit holds information of an actual size of the ejection opening at the distal end portion of the endoscope.

Preferably, the region detecting unit detects the region of the water jet that is in contact with the subject by extracting, from the endoscopic image, a region to which the water jet is ejected, on the basis of a position and direction in which the water jet is ejected in the endoscopic image, the position and direction being determined in accordance with a positional relationship between an observation window and the ejection opening at the distal end portion of the endoscope.

Preferably, the region detecting unit detects the region of the water jet that is in contact with the subject in accordance with a difference in a ratio of pixel values of individual pixels between the subject and a region to which the water jet is ejected in a spectral image having two color components of the endoscopic image.

Preferably, the ejection opening at the distal end portion of the endoscope is a dedicated ejection opening from which the water jet is ejected.

Preferably, the ejection opening at the distal end portion of the endoscope is a forceps outlet at the distal end portion of the endoscope.

Preferably, the region detecting unit starts detecting the region of the artificial object or the water jet that is in contact with the subject in response to an instruction to start detecting the region, and finishes detecting the region in response to an instruction to finish detecting the region.

Preferably, the region detecting unit starts detecting the region of the artificial object or the water jet that is in contact with the subject in response to an instruction to start detecting the region, and finishes detecting the region after a predetermined time period elapses from when the endoscopic image and the scales are combined and displayed on the display unit.

The present invention also provides an image processing method including a step of holding, with a size information holding unit, information of an actual size of a region of an artificial object that extends outward from a distal end portion of an endoscope and is in contact with a subject or a region of a water jet that is ejected from an ejection opening at the distal end portion of the endoscope and is in contact with the subject; a step of detecting, with a region detecting unit, the region of the artificial object or the water jet that is in contact with the subject from an endoscopic image of the subject captured by an imaging unit from the distal end portion of the endoscope; a step of calculating in number of pixels, with an imaging size calculating unit, an imaging size of the region of the artificial object or the water jet that is in contact with the subject in the endoscopic image; a step of calculating, with a pixel size calculating unit, an actual size corresponding to one pixel of the endoscopic image on the basis of the imaging size and the information of the actual size; a step of generating, with a scale generating unit, scales indicating an actual size of the subject in the endoscopic image on the basis of the actual size corresponding to the one pixel of the endoscopic image; and a step of performing, with a control unit, control to combine the endoscopic image and the scales and to display, on a display unit, the endoscopic image and the scales that have been combined.

Preferably, the artificial object is a hood that is cylindrical-shaped and has opening portions at both ends thereof, one of the opening portions being fitted and attached to the distal end portion of the endoscope, the size information holding unit holds information of an actual size of the other opening portion of the hood that is in contact with the subject, the region detecting unit detects, from the endoscopic image, the other opening portion of the hood that is in contact with the subject, and the imaging size calculating unit calculates, in number of pixels, an imaging size of the other opening portion of the hood that is in contact with the subject in the endoscopic image.

Preferably, the artificial object is a surgical instrument that extends outward from a forceps outlet at the distal end portion of the endoscope, the size information holding unit holds information of an actual size of a tip portion of the surgical instrument, the region detecting unit detects, from the endoscopic image, the tip portion of the surgical instrument that is in contact with the subject, and the imaging size calculating unit calculates, in number of pixels, an imaging size of the tip portion of the surgical instrument that is in contact with the subject in the endoscopic image.

Preferably, the size information holding unit holds information of an actual size of the ejection opening at the distal end portion of the endoscope, the region detecting unit detects, from the endoscopic image, the region of the water jet that is in contact with the subject, and the imaging size calculating unit calculates, in number of pixels, the imaging size of the region of the water jet that is in contact with the subject in the endoscopic image.

The present invention also provides a non-transitory computer-readable recording medium on which a program is recorded, the program causing a computer to execute the individual steps of the image processing method described above.

According to the present invention, the size of a lesion portion or the like can be easily measured by using an endoscopic image captured through a normal operation, not by using an endoscopic image captured for the purpose of measuring the size of a lesion portion or the like.

DESCRIPTION OF THE PREFERRED EMBODIMENTS

Hereinafter, an endoscopic diagnosis apparatus, image processing method, program, and a non-transitory recording medium according to the present invention will be described in detail on the basis of preferred embodiments illustrated in the attached drawings.

Figure 1:
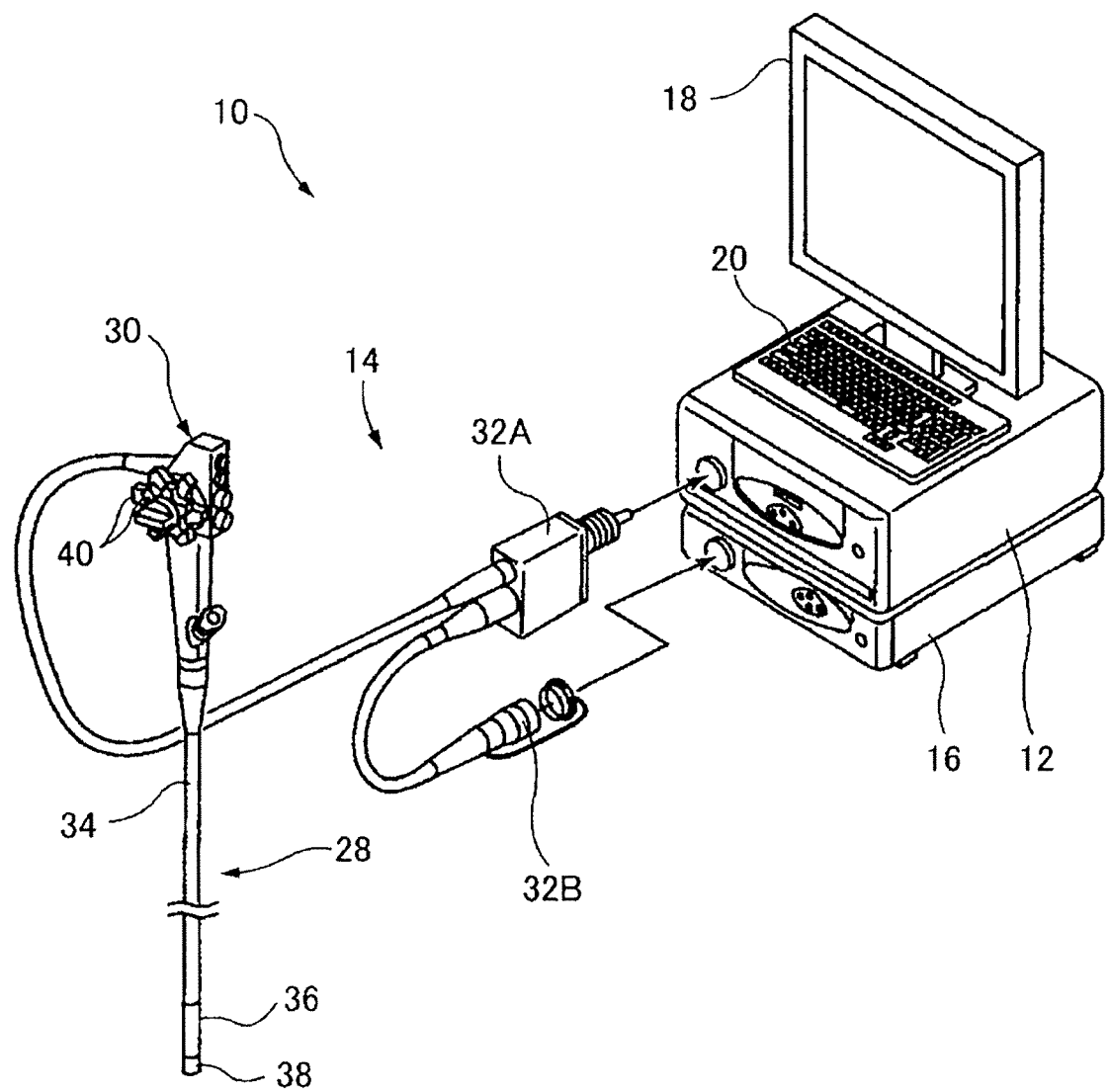
FIG. 1 is an external view of an embodiment illustrating the configuration of an endoscopic diagnosis apparatus according to the present invention.
Figure 2:
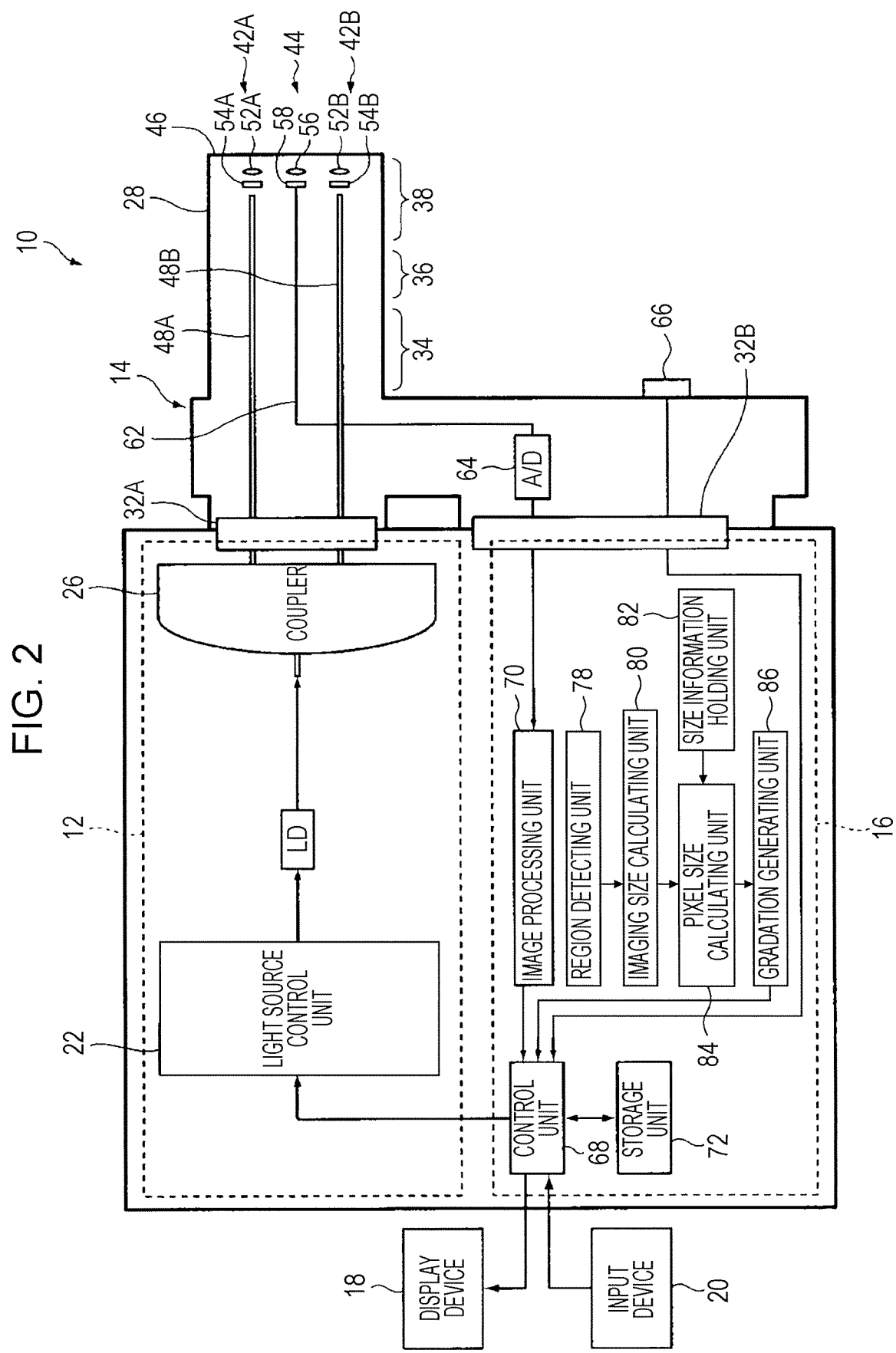
FIG. 2 is a block diagram illustrating the internal configuration of the endoscopic diagnosis apparatus illustrated in FIG. 1.

FIG. 1 is an external view of an embodiment illustrating the configuration of the endoscopic diagnosis apparatus according to the present invention, and FIG. 2 is a block diagram illustrating the internal configuration thereof. The endoscopic diagnosis apparatus 10 illustrated in these figures is constituted by a light source device 12, an endoscope 14 that captures an endoscopic image of a region of interest of a subject by using light emitted by the light source device 12, a processor device 16 that performs image processing on the endoscopic image captured by the endoscope 14, a display device 18 that displays the endoscopic image that has undergone the image processing and has been output from the processor device 16, and an input device 20 that receives an input operation.

The light source device 12 is constituted by a light source control unit 22, a laser light source LD, and a coupler (optical splitter) 26.

In this embodiment, the laser light source LD emits narrowband light having a center wavelength of 445 nm in a predetermined blue wavelength range (for example, the center wavelength ±10 nm). The laser light source LD is a light source that emits, as illumination light, excitation light for causing fluorescent bodies described below to generate white light (pseudo white light). ON/OFF (light-up/light-down) control and light amount control of the laser light source LD are performed by the light source control unit 22, which is controlled by a control unit 68 of the processor device 16 described below.

As the laser light source LD, an InGaN-based laser diode of a broad area type can be used. Alternatively, an InGaNAs-based laser diode, a GaNAs-based laser diode, or the like can be used.

A white light source for generating white light is not limited to a combination of excitation light and fluorescent bodies, and any light source that emits white light may be used. For example, a xenon lamp, halogen lamp, white LED (light-emitting diode), or the like can be used. The wavelength of the laser light emitted by the laser light source LD is not limited to the foregoing example, and laser light with a wavelength that plays a similar role can be selected as appropriate.

The laser light emitted by the laser light source LD enters an optical fiber through a condenser lens (not illustrated) and is then transmitted to a connector section 32A after being split into two branches of light by the coupler 26. The coupler 26 is constituted by a half-mirror, reflection minor, or the like.

The endoscope 14 is an electronic endoscope having an illumination optical system that emits two branches (two beams) of illumination light from a distal end surface 46 of an endoscope insertion section 28 that is to be inserted into a subject, and an imaging optical system of a single system (single lens) type that captures an endoscopic image of a region of interest. The endoscope 14 includes the endoscope insertion section 28, an operation section 30 that is operated to bend a distal end of the endoscope insertion section 28 or to perform observation, and connector sections 32A and 32B for connecting the endoscope 14 to the light source device 12 and the processor device 16 in a detachable manner.

The endoscope insertion section 28 is constituted by a flexible portion 34 having flexibility, a bending portion 36, and a distal end portion (hereinafter also referred to as an endoscope distal end portion) 38.

The bending portion 36 is disposed between the flexible portion 34 and the distal end portion 38 and is configured to be freely bent by a rotational operation of an angle knob 40 located at the operation section 30. The bending portion 36 can be bent in an arbitrary direction or at an arbitrary angle in accordance with a portion or the like of a subject for which the endoscope 14 is used, and accordingly the endoscope distal end portion 38 can be oriented toward a desired portion of interest.

Figure 3:
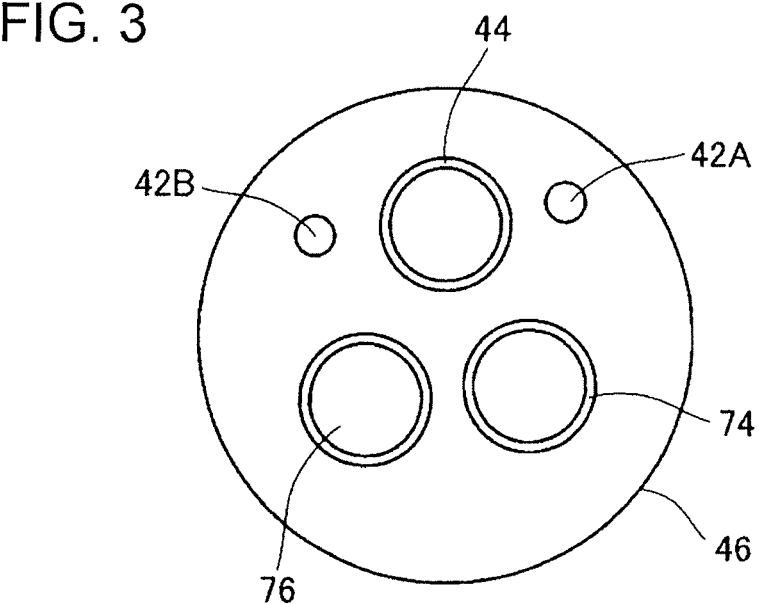
FIG. 3 is a conceptual diagram illustrating the configuration of a distal end portion of an endoscope.

As illustrated in FIG. 3, two illumination windows 42A and 42B for emitting light onto a region of interest, one observation window 44 for gathering reflected light from the region of interest, a forceps outlet 74 serving as an exit for a surgical instrument or the like that is inserted into a forceps channel disposed inside the endoscope insertion section 28, an air/water supply channel opening 76 serving as an exit of an air/water supply channel, and so forth are located on the distal end surface 46 of the endoscope insertion section 28.

The observation window 44, the forceps outlet 74, and the air/water supply channel opening 76 are located in a center portion of the distal end surface 46. The illumination windows 42A and 42B are located on both sides of the observation window 44 so as to sandwich the observation window 44.

An optical fiber 48A is accommodated behind the illumination window 42A. The optical fiber 48A extends from the light source device 12 to the endoscope distal end portion 38 through the connector section 32A. A fluorescent body 54A is located in front of a tip portion (on the illumination window 42A side) of the optical fiber 48A, and in addition an optical system such as a lens 52A is attached in front of the fluorescent body 54A. Likewise, an optical fiber 48B is accommodated behind the illumination window 42B. A fluorescent body 54B and an optical system such as a lens 52B are located in front of a tip portion of the optical fiber 48B.

The fluorescent bodies 54A and 54B contain a plurality of kinds of fluorescent substances (for example, a YAG-based fluorescent substance or a fluorescent substance such as BAM ($BaMgAl_{10}O_{17}$)) that absorb a part of blue laser light emitted by the laser light source LD and that are excited to emit light in the green to yellow spectrum. When the fluorescent bodies 54A and 54B are irradiated with excitation light, light in the green to yellow spectrum (fluorescent light) emitted by the fluorescent bodies 54A and 54B as a result of excitation is combined with blue laser light that has passed through the fluorescent bodies 54A and 54B without being absorbed, and thereby white light (pseudo white light) for observation is generated.

Figure 4:
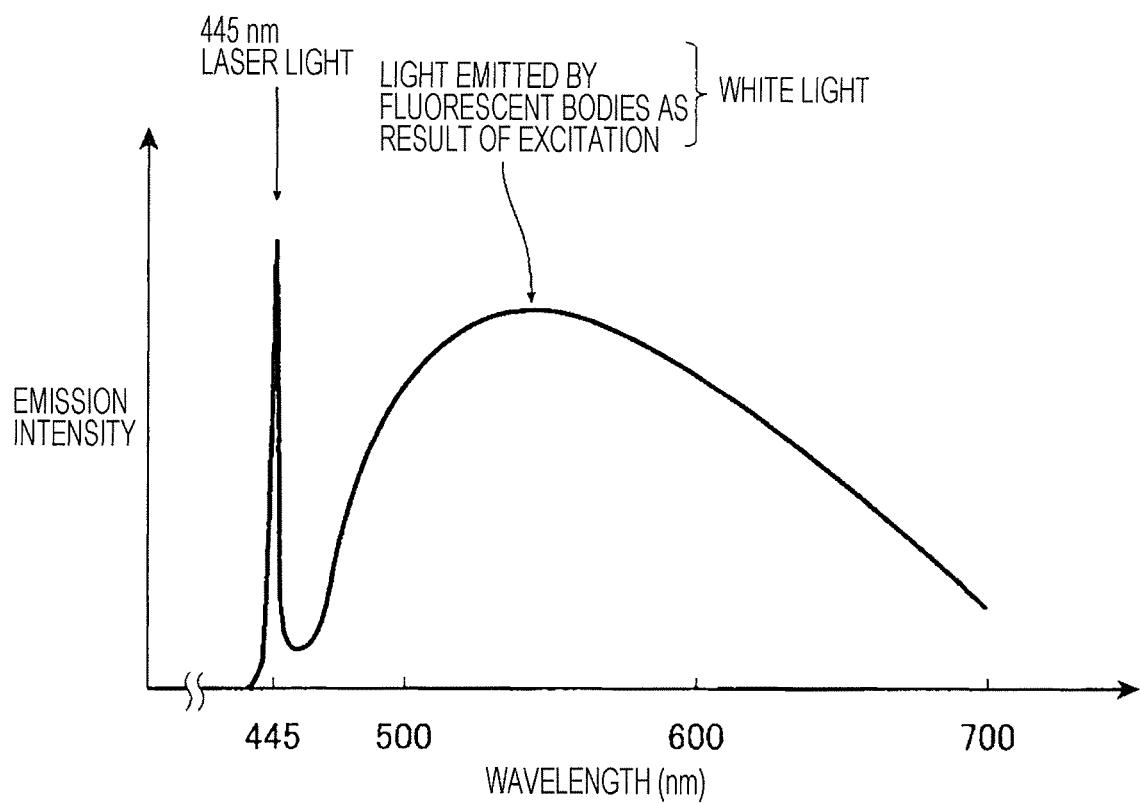
FIG. 4 is a graph illustrating an emission spectrum of blue laser light emitted by a blue laser light source and of light obtained by converting the wavelength of the blue laser light by using fluorescent bodies.

FIG. 4 is a graph illustrating an emission spectrum of blue laser light emitted by the blue laser light source and of light obtained by converting the wavelength of the blue laser light by using fluorescent bodies. The blue laser light emitted by the laser light source LD is expressed by an emission line having a center wavelength of 445 nm, and the light emitted by the fluorescent bodies 54A and 54B as a result of excitation caused by the blue laser light has a spectral intensity distribution in which the emission intensity increases in a wavelength range of about 450 to 700 nm. Composite light of the light emitted as a result of excitation and the blue laser light forms the foregoing pseudo white light.

The white light according to the present invention is not limited to light strictly including all wavelength components of visible light and may be, for example, light including light in specific wavelength bands, for example, wavelength bands of R (red), G (green), and B (blue) as reference colors, as well as the foregoing pseudo white light. That is, the white light according to the present invention includes, in a broad sense, light including green to red wavelength components, light including blue to green wavelength components, and the like.

In the illumination optical system, the configuration and operation of the illumination window 42A side and the illumination window 42B side are equivalent to each other, and basically equivalent illumination light beams are simultaneously emitted from the illumination windows 42A and 42B. Alternatively, different illumination light beams may be emitted from the illumination windows 42A and 42B. It is not required to have an illumination optical system that emits two branches of illumination light. For example, an equivalent function may be implemented by an illumination optical system that emits one or four branches of illumination light.

An optical system, such as an objective lens unit 56, for gathering image light of a region of interest of a subject is disposed behind the observation window 44. Furthermore, an imaging device 58, such as a CCD (Charge Coupled Device) image sensor or CMOS (Complementary Metal-Oxide Semiconductor) image senor, for obtaining image information on the region of interest is attached behind the objective lens unit 56. The imaging device 58 corresponds to an imaging unit according to the present invention that captures an endoscopic image of a subject from the distal end portion of the endoscope 14.

The imaging device 58 receives, at its imaging surface (light receiving surface), light from the objective lens unit 56, photoelectrically converts the received light, and outputs an imaging signal (analog signal). The imaging surface of the imaging device 58 is provided with red (about 580 to 760 nm), green (about 450 to 630 nm), and blue (about 380 to 510 nm) color filters having spectral transmittance for splitting a wavelength range of about 370 to 720 nm of visible light into three bands, and a plurality of sets of pixels, each set formed of pixels of three colors, R pixel, G pixel, and B pixel, are arranged in a matrix on the imaging surface.

The light beams guided by the optical fibers 48A and 48B from the light source device 12 are emitted from the endoscope distal end portion 38 toward a region of interest of a subject. Subsequently, an image depicting a state of the region of interest irradiated with the illumination light is formed on the imaging surface of the imaging device 58 by the objective lens unit 56 and is captured through photoelectric conversion by the imaging device 58. An imaging signal (analog signal) of the captured endoscopic image of the region of interest of the subject is output from the imaging device 58.

The imaging signal (analog signal) of the endoscopic image output from the imaging device 58 is input to an A/D converter 64 through a scope cable 62. The A/D converter 64 converts the imaging signal (analog signal) from the imaging device 58 to an image signal (digital signal). The image signal obtained through the conversion is input to an image processing unit 70 of the processor device 16 through the connector section 32B.

The processor device 16 includes the image processing unit 70, a region detecting unit 78, an imaging size calculating unit 80, a size information holding unit 82, a pixel size calculating unit 84, a scale generating unit 86, the control unit 68, and a storage unit 72. The display device 18 and the input device 20 are connected to the control unit 68. The processor device 16 controls the light source control unit 22 of the light source device 12 and also performs image processing on an image signal of an endoscopic image received from the endoscope 14 and outputs the endoscopic image that has undergone the image processing to the display device 18, in response to an instruction input through an imaging switch 66 of the endoscope 14 or the input device 20. The display device 18 corresponds to a display unit according to the present invention that displays an endoscopic image.

The image processing unit 70 performs various kinds of image processing, set in advance, on an image signal of an endoscopic image received from the endoscope 14 and outputs an image signal of the endoscopic image that has undergone the image processing. The image signal of the endoscopic image that has undergone the image processing is transmitted to the control unit 68.

The region detecting unit 78 detects, from an endoscopic image corresponding to the image signal of the endoscopic image, a region of an artificial object that extends outward from the distal end portion of the endoscope 14 and is in contact with a subject or a region of a water jet that is ejected from an ejection opening at the distal end portion of the endoscope 14 and is in contact with the subject.

Here, the artificial object is not limited as long as the actual size of a region that is in contact with a subject is known and as long as the artificial object extends outward from the distal end portion of the endoscope 14 so as to be imaged together with the subject at the time of capturing an endoscopic image. An example of the artificial object may be a hood, surgical instrument, or the like.

Figure 5A:
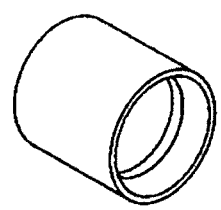
FIG. 5A is a conceptual diagram illustrating the configuration of a hood to be attached to the distal end portion of the endoscope.
Figure 5B:
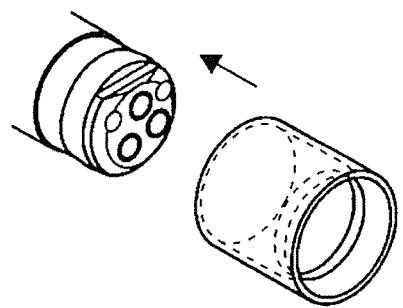
FIG. 5B is a conceptual diagram illustrating a state of attaching the hood illustrated in FIG. 5A to the distal end portion of the endoscope.

As illustrated in FIG. 5A, the hood is cylindrical-shaped, has opening portions at both ends thereof, and is used in the case of, for example, capturing an endoscopic image while fixing the distance between the distal end portion of the endoscope 14 and a region of interest of a subject. As illustrated in FIG. 5B, one of the opening portions is fitted and attached to the distal end portion of the endoscope 14. The opening portions of the hood may be circular or oval.

The surgical instrument, such as biopsy forceps, is used for various medical procedures while being inserted from a forceps inlet of the endoscope 14 and extended outward from the forceps outlet 74 at the distal end portion of the endoscope 14.

The water jet is ejected from the ejection opening at the distal end portion of the endoscope 14 in the case of, for example, washing a surface of a subject.

The ejection opening at the distal end portion of the endoscope 14 from which a water jet is ejected is not limited as long as the actual size thereof is known and as long as a water jet can be ejected from the distal end portion of the endoscope 14. For example, the ejection opening may be a dedicated ejection opening from which a water jet is ejected, such as the air/water supply channel opening 76, or may be the forceps outlet 74 at the distal end portion of the endoscope 14. Alternatively, a surgical instrument for ejecting a water jet may be inserted from the forceps inlet of the endoscope 14 and may be protruded from the forceps outlet 74 at the distal end portion so as to eject a water jet. The diameters or the like of the air/water supply channel opening 76, the forceps outlet 74, and the ejection opening for the surgical instrument for ejecting a water jet are known.

A method for detecting, by using the region detecting unit 78, a region of an artificial object or water jet from an endoscopic image is not limited. For example, the region of the artificial object or water jet can be automatically detected by performing image analysis on the endoscopic image.

The imaging size calculating unit 80 calculates, in number of pixels, the imaging size (distance) of the region detected by the region detecting unit 78 of the artificial object or water jet that is in contact with the subject in the endoscopic image.

Here, if the artificial object is a hood, the imaging size of the region of the artificial object in the endoscopic image is the number of pixels corresponding to the diameter or perimeter of the other opening portion of the hood that is in contact with the subject; if the artificial object is a surgical instrument, the imaging size of the region of the artificial object in the endoscopic image is the number of pixels corresponding to the diameter of a cross-section of a tip portion of the surgical instrument that is in contact with the subject; and in the case of the water jet, the imaging size of the region of the water jet in the endoscopic image is the number of pixels corresponding to the diameter of a cross-section of the water jet that is in contact with the subject. The imaging size is not limited thereto, and the size of a region whose actual size is known and in which an artificial object or water jet is in contact with a subject can be calculated, in number of pixels, as the imaging size of the region of the artificial object or water jet in the endoscopic image.

The size information holding unit 82 holds information of the actual size (distance) of the region of the artificial object or water jet that is in contact with the subject.

Here, if the artificial object is a hood, the actual size of the region in which the artificial object is in contact with the subject is the actual diameter or perimeter of the other opening portion of the hood that is in contact with the subject; if the artificial object is a surgical instrument, the actual size of the region in which the artificial object is in contact with the subject is the actual diameter of a cross-section of a tip portion of the surgical instrument that is in contact with the subject; and in the case of the water jet, the actual size of the region in which water jet is in contact with the subject is the actual diameter of a cross-section of the water jet that is in contact with the subject, that is, the actual diameter of the ejection opening.

The pixel size calculating unit 84 calculates the actual size (distance) corresponding to one pixel of the endoscopic image on the basis of the imaging size calculated by the imaging size calculating unit 80 in number of pixels and the information of the actual size held by the size information holding unit 82.

For example, if the imaging size is X pixels and the actual size is Y mm, the actual size corresponding to one pixel of the endoscopic image can be calculated as Y/X.

The scale generating unit 86 generates scales, such as a scale bar, indicating the actual size of the subject in the endoscopic image, on the basis of the actual size corresponding to one pixel of the endoscopic image calculated by the pixel size calculating unit 84.

The control unit 68 performs control to display on the display device 18 the endoscopic image that has undergone image processing. In this case, the endoscopic image and the scales generated by the scale generating unit 86 can be combined and displayed on the display device 18 under control of the control unit 68. In addition, the control unit 68 controls the operation of the light source control unit 22 of the light source device 12 and performs, for example, control to store endoscopic images in units of images (in units of frames) in the storage unit 72 in response to an instruction from the imaging switch 66 of the endoscope 14 or the input device 20.

Next, a description will be given of an operation of the endoscopic diagnosis apparatus 10.

First, a description will be given of an operation in the case of capturing an endoscopic image.

At the time of capturing an endoscopic image, the laser light source LD is lit up with a constant amount of light set in advance under control of the light source control unit 22. Laser light having a center wavelength of 445 nm and emitted by the laser light source LD is applied onto the fluorescent bodies 54A and 54B, and white light is emitted by the fluorescent bodies 54A and 54B. The white light emitted by the fluorescent bodies 54A and 54B is applied onto a subject, the reflected light thereof is received by the imaging device 58, and thereby an endoscopic image of a region of interest of the subject is captured.

An imaging signal (analog signal) of the endoscopic image output from the imaging device 58 is converted to an image signal (digital signal) by the A/D converter 64, various kinds of image processing are performed by the image processing unit 70, and the image signal of the endoscopic image that has undergone the image processing is output. Subsequently, the control unit 68 causes the display device 18 to display an endoscopic image corresponding to the image signal of the endoscopic image that has undergone the image processing, and if necessary, causes the storage unit 72 to store the image signal of the endoscopic image.

Next, a description will be given of an operation in the case of measuring the actual size of a region of interest of a subject.

First, a description will be given of, as a first embodiment, the case of measuring the actual size of a subject in an endoscopic image by using the hood attached to the distal end portion of the endoscope 14.

First, an operator of the endoscopic diagnosis apparatus 10 inputs through the input device 20 information of the actual size of the other opening portion of the hood attached to the distal end portion of the endoscope 14. The information of the actual size of the other opening portion of the hood is held by the size information holding unit 82.

Figure 6A:
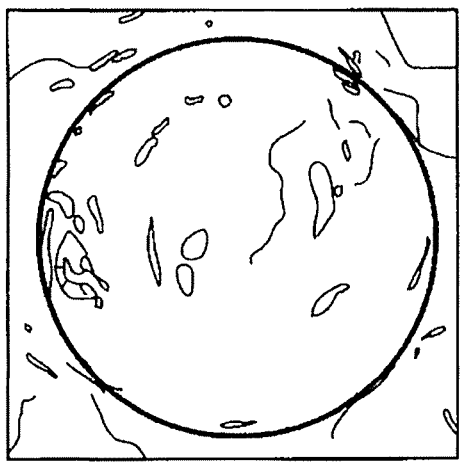
FIG. 6A is a conceptual diagram illustrating an endoscopic image in which the hood is imaged.

Subsequently, the operator inserts the endoscope 14 whose distal end portion is attached with the transparent hood into a subject and moves the endoscope 14 to a region of interest while checking an endoscopic image displayed on the display device 18, and then the other opening portion of the hood comes in contact with a surface of the region of interest of the subject, as illustrated in FIG. 6A.

Subsequently, the operator presses a button or the like located in the operation section 30 of the endoscope 14 to input an instruction to start detecting the other opening portion of the hood.

Upon input of the instruction to start detecting the other opening portion of the hood, the region detecting unit 78 starts detecting the other opening portion of the hood that is in contact with the subject from the endoscopic image.

The region detecting unit 78 detects the other opening portion of the hood that is in contact with the subject by performing image analysis and extracting a circular edge from a peripheral portion of the endoscopic image under the assumption that the other opening portion of the hood is imaged in a circular shape in the peripheral portion of the endoscopic image.

Subsequently, the imaging size calculating unit 80 calculates, in number of pixels, the imaging size of the other opening portion of the hood that is in contact with the subject in the endoscopic image, for example, the imaging diameter of the other opening portion of the hood in the endoscopic image.

Subsequently, the pixel size calculating unit 84 calculates the actual size corresponding to one pixel of the endoscopic image on the basis of the imaging size and the information of the actual size of the other opening portion of the hood held by the size information holding unit 82.

Subsequently, the scale generating unit 86 generates scales indicating the actual size of the subject in the endoscopic image on the basis of the actual size corresponding to one pixel of the endoscopic image.

Figure 6B:
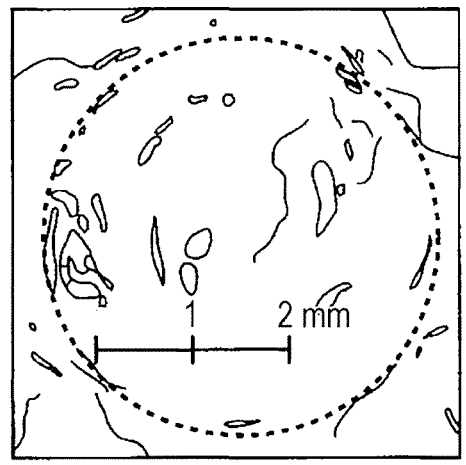
FIG. 6B is a conceptual diagram illustrating a state where the endoscopic image illustrated in FIG. 6A and scales are combined.

Subsequently, under control of the control unit 68, the endoscopic image and the scales are combined and displayed on the display device 18. As illustrated in FIG. 6B, for example, a scale bar in which the length of 1 mm can be seen is displayed as the scales on the screen of the display device 18. In FIG. 6B, the other opening portion detected by the region detecting unit 78 of the hood that is in contact with the subject is illustrated with being encompassed by a dotted line.

Subsequently, the operator presses a button or the like located in the operation section 30 of the endoscope 14 to input an instruction to finish detecting the other opening portion of the hood to the endoscopic diagnosis apparatus 10.

Upon input of the instruction to finish detecting the other opening portion of the hood, the region detecting unit 78 finishes detecting the other opening portion of the hood that is in contact with the subject from the endoscopic image. Accordingly, the scales displayed on the display device 18 disappear.

Instead of the finish instruction being input, the region detecting unit 78 may finish detecting the other opening portion of the hood that is in contact with the subject from the endoscopic image after a predetermined time period elapses from when the endoscopic image and the scales are combined and displayed on the display device 18.

Next, a description will be given of, as a second embodiment, the case of measuring the actual size of a subject in an endoscopic image by using a surgical instrument.

As in the case of the first embodiment, the operator inputs through the input device 20 information of the actual size of a tip portion of a surgical instrument extending outward from the forceps outlet 74 at the distal end portion of the endoscope 14. The information is held by the size information holding unit 82.

Figure 7A:
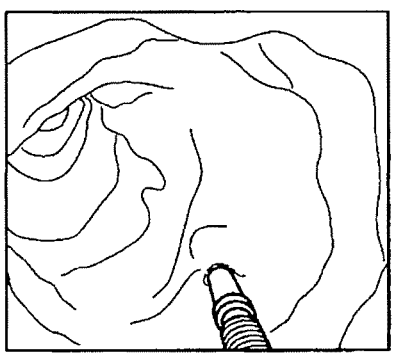
FIG. 7A is a conceptual diagram illustrating an endoscopic image in which a surgical instrument is imaged.

Subsequently, the operator inserts the endoscope 14 into a subject and moves the endoscope 14 to a region of interest while checking an endoscopic image displayed on the display device 18. Subsequently, the operator inserts the surgical instrument from the forceps inlet of the endoscope 14 so that the surgical instrument is extended outward from the forceps outlet 74 at the distal end portion of the endoscope 14, and the tip portion of the surgical instrument comes in contact with a surface of the region of interest of the subject, as illustrated in FIG. 7A.

Subsequently, the operator presses a button or the like located in the operation section 30 of the endoscope 14 to input an instruction to start detecting the tip portion of the surgical instrument to the endoscopic diagnosis apparatus 10.

Upon input of the instruction to start detecting the tip portion of the surgical instrument, the region detecting unit 78 starts detecting the tip portion of the surgical instrument that is in contact with the subject from the endoscopic image.

Here, the surgical instrument is inserted to the forceps channel of the endoscope 14. The positional relationship between the observation window 44 and the forceps outlet 74 at the distal end portion of the endoscope 14 is fixed. Thus, when the surgical instrument is extended outward from the distal end portion of the endoscope 14, the surgical instrument appears at a determined position in a determined direction in the endoscopic image without exception.

Applying this property, the region detecting unit 78 is capable of detecting the tip portion of the surgical instrument that is in contact with the subject by performing image analysis and extracting, from the endoscopic image, a region in which the surgical instrument extends, on the basis of the position and direction in which the surgical instrument extends in the endoscopic image, the position and direction being determined in accordance with the positional relationship between the observation window 44 and the forceps outlet 74 at the distal end portion of the endoscope 14.

Figure 8:
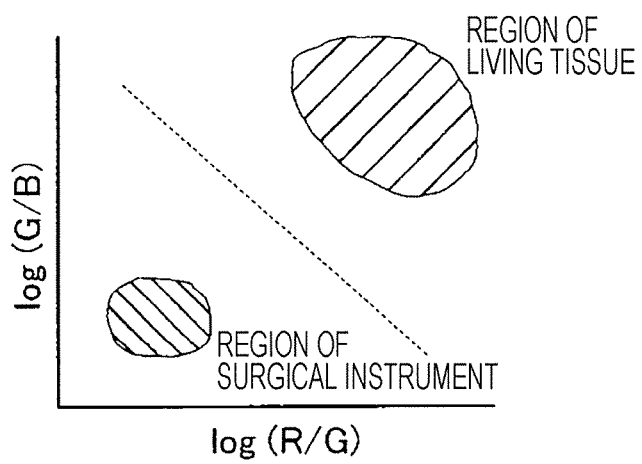
FIG. 8 is a graph illustrating a difference in a ratio of pixel values of individual pixels in a spectral image having individual color components between a region in which the surgical instrument extends and a region of living tissue of a subject.

In the region in which the surgical instrument extends in the endoscopic image, the ratio of pixel values of individual pixels in a spectral image having individual color components of RGB or the like is completely different from that in a region of living tissue of the subject. The region of living tissue of the subject is reddish, where the amount of R component is the largest, the amount of G component is the second largest, and the amount of B component is the smallest (R component>G component>B component). On the other hand, the region in which the surgical instrument extends is white or light gray, has a ratio of individual color components of RGB of about 1:1:1, and has large pixel values of the individual color components. Thus, as illustrated in the graph in FIG. 8, in which the lateral axis represents log (R/G) and the vertical axis represents log (G/B) as the ratio of the individual color components of RGB, the pixel values of the region of living tissue of the subject are included in an upper-right region of the graph, whereas the pixel values of the region in which the surgical instrument extends are included in a lower-left region of the graph.

Applying this property, the region detecting unit 78 may detect the tip portion of the surgical instrument that is in contact with the subject in accordance with a difference in the ratio of pixel values of individual pixels between the subject and the region in which the surgical instrument extends in a spectral image having two color components of the endoscopic image. Accordingly, the tip portion of the surgical instrument that is in contact with the subject can be detected more accurately.

This property may also be applied to the case of a special optical image that is captured by using special light such as short-wavelength laser light of BLI (Blue Laser Imaging), as well as a spectral image having individual color components of a white light image that is captured by using white light.

Subsequently, the imaging size calculating unit 80 calculates, in number of pixels, the imaging size of the tip portion of the surgical instrument that is in contact with the subject in the endoscopic image, that is, the imaging diameter of the cross-section of the tip portion of the surgical instrument in the endoscopic image.

Subsequently, the pixel size calculating unit 84 calculates the actual size corresponding to one pixel of the endoscopic image on the basis of the imaging size and the information of the actual size of the tip portion of the surgical instrument held by the size information holding unit 82.

Figure 7B:
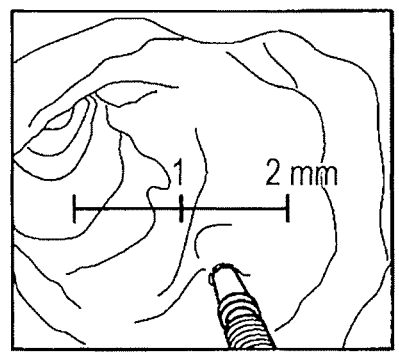
FIG. 7B is a conceptual diagram illustrating a state where the endoscopic image illustrated in FIG. 7A and scales are combined.

The subsequent operation is similar to that in the case of the first embodiment. Under control of the control unit 68, the endoscopic image and the scales are combined, and a scale bar in which the length of 1 mm can be seen is displayed on the screen of the display device 18 as illustrated in FIG. 7B, for example.

Next, a description will be given of, as a third embodiment, the case of measuring the actual length of a subject in an endoscopic image by using a water jet.

As in the case of the first embodiment, the operator inputs through the input device 20 information of the actual size of the ejection opening from which a water jet is ejected at the distal end portion of the endoscope 14. The information is held by the size information holding unit 82.

Figure 9:
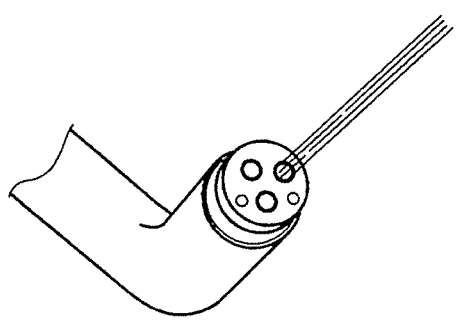
FIG. 9 is a conceptual diagram illustrating a state where a water jet is ejected from an ejection opening at the distal end portion of the endoscope.

Subsequently, the operator inserts the endoscope 14 into a subject and moves the endoscope 14 to a region of interest while checking an endoscopic image displayed on the display device 18. Subsequently, a water jet is ejected from the ejection opening at the distal end portion of the endoscope 14 to a surface of the region of interest of the subject, as illustrated in FIG. 9.

Subsequently, the operator presses a button or the like located in the operation section 30 of the endoscope 14 to input an instruction to start detecting a region of the water jet to the endoscopic diagnosis apparatus 10.

Upon input of the instruction to start detecting the region of the water jet, the region detecting unit 78 starts detecting the region of the water jet that is in contact with the subject from the endoscopic image.

Here, the diameter of a water column of the water jet largely depends on the diameter of a water channel, that is, the size of the ejection opening at the distal end portion of the endoscope 14. The positional relationship between the observation window 44 and the ejection opening at the distal end portion of the endoscope 14 is fixed. Thus, when a water jet is ejected from the ejection opening at the distal end portion of the endoscope 14, the water jet appears at a determined position in a determined direction in the endoscopic image without exception.

Applying this property, the region detecting unit 78 is capable of detecting the region of the water jet that is in contact with the subject by performing image analysis and extracting, from the endoscopic image, the region to which the water jet is ejected, on the basis of the position and direction in which the water jet is ejected in the endoscopic image, the position and direction being determined in accordance with the positional relationship between the observation window 44 and the ejection opening at the distal end portion of the endoscope 14.

When the water jet hits on the subject, it splashes and spatters. Thus, the region of the water jet that is in contact with the subject can be detected by detecting an interface between a region in which the water jet linearly splashes and a region in which the water jet hits on the subject to splash and spatter.

In the region to which the water jet is ejected in the endoscopic image, the ratio of pixel values of individual pixels in a spectral image having individual color components of RGB (red, green, blue) or the like is completely different from that in a region of living tissue of the subject, as in the case of the second embodiment.

Applying this property, the region detecting unit 78 may detect the region of the water jet that is in contact with the subject in accordance with a difference in the ratio of pixel values of individual pixels between the subject and the region to which the water jet is ejected in a spectral image having two color components of the endoscopic image. Accordingly, the region of the water jet that is in contact with the subject can be detected more accurately.

Subsequently, the imaging size calculating unit 80 calculates, in number of pixels, the imaging size of the region of the water jet that is in contact with the subject in the endoscopic image, that is, the imaging diameter of the cross-section of the water jet in the endoscopic image.

Subsequently, the pixel size calculating unit 84 calculates the actual size corresponding to one pixel of the endoscopic image on the basis of the imaging size and the information of the actual size of the ejection opening held by the size information holding unit 82.

The subsequent operation is similar to that in the case of the first embodiment. Under control of the control unit 68, the endoscopic image and the scales are combined, and a scale bar in which the length of 1 mm can be seen is displayed on the screen of the display device 18.

In this way, the endoscopic diagnosis apparatus 10 is capable of easily measuring the size of a lesion portion or the like by using an endoscopic image captured through a normal operation, not by using an endoscopic image captured for the purpose of measuring the size of a lesion portion or the like.

In the apparatus according to the present invention, each element included in the apparatus may be constituted by dedicated hardware, or each element may be constituted by a programmed computer.

The method according to the present invention can be implemented by a program that causes a computer to execute individual steps of the method, as described above. Furthermore, a non-transitory computer-readable recording medium on which the program is recorded can be provided.

The present invention is basically as above.

The present invention has been described in detail above. The present invention is not limited to the above-described embodiments, and various improvements and changes can of course be made without deviating from the gist of the present invention.

REFERENCE SIGNS LIST 10 endoscopic diagnosis apparatus
12 light source device
14 endoscope
16 processor device
18 display device
20 input device
22 light source control unit
26 coupler (optical splitter)
28 endoscope insertion section
30 operation section
32A, 32B connector section
34 flexible portion
36 bending portion
38 distal end portion
40 angle knob
42A, 42B illumination window
44 observation window
46 distal end surface
48A, 48B optical fiber
52A, 52B lens
54A, 54B fluorescent body
56 objective lens unit
58 imaging device
62 scope cable
64 A/D converter
66 imaging switch
68 control unit
70 image processing unit
72 storage unit
74 forceps outlet
76 air/water supply channel opening
78 region detecting unit
80 imaging size calculating unit
82 size information holding unit
84 pixel size calculating unit
86 scale generating unit
LD laser light source

What is claimed is:

1. An endoscopic diagnosis apparatus comprising:
an imaging device that captures an endoscopic image of a subject from a distal end portion of an endoscope;
a display device that displays the endoscopic image; and
a processor configured to:
detect, from the endoscopic image, a region of an artificial object that extends outward from the distal end portion of the endoscope and is in contact with the subject or a region of a water jet that is ejected from an ejection opening at the distal end portion of the endoscope and is in contact with the subject;
calculate, in number of pixels, an imaging size of the region of the artificial object or the water jet that is in contact with the subject in the endoscopic image;
hold information of an actual size of the region of the artificial object or the water jet that is in contact with the subject;
calculate an actual size corresponding to one pixel of the endoscopic image on the basis of the imaging size and the information of the actual size;
generate scales indicating an actual size of the subject in the endoscopic image on the basis of the actual size corresponding to the one pixel of the endoscopic image; and
perform control to combine the endoscopic image and the scales and to display, on the display device, the endoscopic image and the scales that have been combined.

2. The endoscopic diagnosis apparatus according to claim 1, wherein
the artificial object is a hood that is cylindrical-shaped and has opening portions at both ends thereof, one of the opening portions being fitted and attached to the distal end portion of the endoscope,
the processor detects, from the endoscopic image, the other opening portion of the hood that is in contact with the subject,
the processor calculates, in number of pixels, an imaging size of the other opening portion of the hood that is in contact with the subject in the endoscopic image, and
the processor holds information of an actual size of the other opening portion of the hood that is in contact with the subject.

3. The endoscopic diagnosis apparatus according to claim 2, wherein
the processor detects the other opening portion of the hood that is in contact with the subject by extracting a circular edge from a peripheral portion of the endoscopic image.

4. The endoscopic diagnosis apparatus according to claim 1, wherein
the artificial object is a surgical instrument that extends outward from a forceps outlet at the distal end portion of the endoscope,
the processor detects, from the endoscopic image, a tip portion of the surgical instrument that is in contact with the subject,
the processor calculates, in number of pixels, an imaging size of the tip portion of the surgical instrument that is in contact with the subject in the endoscopic image, and
the processor holds information of an actual size of the tip portion of the surgical instrument.

5. The endoscopic diagnosis apparatus according to claim 4, wherein
the processor detects the tip portion of the surgical instrument that is in contact with the subject by extracting, from the endoscopic image, a region in which the surgical instrument extends, on the basis of a position and direction in which the surgical instrument extends in the endoscopic image, the position and direction being determined in accordance with a positional relationship between an observation window and the forceps outlet at the distal end portion of the endoscope.

6. The endoscopic diagnosis apparatus according to claim 4, wherein
the processor detects the tip portion of the surgical instrument that is in contact with the subject in accordance with a difference in a ratio of pixel values of individual pixels between the subject and a region in which the surgical instrument extends in a spectral image having two color components of the endoscopic image.

7. The endoscopic diagnosis apparatus according to claim 1, wherein
the processor detects, from the endoscopic image, the region of the water jet that is in contact with the subject,
the processor calculates, in number of pixels, the imaging size of the region of the water jet that is in contact with the subject in the endoscopic image, and
the processor holds information of an actual size of the ejection opening at the distal end portion of the endoscope.

8. The endoscopic diagnosis apparatus according to claim 7, wherein
the processor detects the region of the water jet that is in contact with the subject by extracting, from the endoscopic image, a region to which the water jet is ejected, on the basis of a position and direction in which the water jet is ejected in the endoscopic image, the position and direction being determined in accordance with a positional relationship between an observation window and the ejection opening at the distal end portion of the endoscope.

9. The endoscopic diagnosis apparatus according to claim 8, wherein
the ejection opening at the distal end portion of the endoscope is a dedicated ejection opening from which the water jet is ejected.

10. The endoscopic diagnosis apparatus according to claim 7, wherein
the processor detects the region of the water jet that is in contact with the subject in accordance with a difference in a ratio of pixel values of individual pixels between the subject and a region to which the water jet is ejected in a spectral image having two color components of the endoscopic image.

11. The endoscopic diagnosis apparatus according to claim 10, wherein
the ejection opening at the distal end portion of the endoscope is a dedicated ejection opening from which the water jet is ejected.

12. The endoscopic diagnosis apparatus according to claim 7, wherein
the ejection opening at the distal end portion of the endoscope is a dedicated ejection opening from which the water jet is ejected.

13. The endoscopic diagnosis apparatus according to claim 7, wherein the ejection opening at the distal end portion of the endoscope is a forceps outlet at the distal end portion of the endoscope.

14. The endoscopic diagnosis apparatus according to claim 1, wherein
the processor starts detecting the region of the artificial object or the water jet that is in contact with the subject in response to an instruction to start detecting the region, and finishes detecting the region in response to an instruction to finish detecting the region.

15. The endoscopic diagnosis apparatus according to claim 1, wherein
the processor starts detecting the region of the artificial object or the water jet that is in contact with the subject in response to an instruction to start detecting the region, and finishes detecting the region after a predetermined time period elapses from when the endoscopic image and the scales are combined and displayed on the display device.

* * * * *